United States Patent
Clements et al.

(10) Patent No.: US 6,710,203 B2
(45) Date of Patent: Mar. 23, 2004

(54) PREPARATION OF HYDROXYALKYLCARBAMATES FROM SIX-MEMBERED CYCLIC CARBONATES

(75) Inventors: John H. Clements, Round Rock, TX (US); Howard P. Klein, Austin, TX (US); Edward T. Marquis, Austin, TX (US); James R. Machac, Jr., Lago Vista, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 69 days.

(21) Appl. No.: 09/863,558

(22) Filed: May 23, 2001

(65) Prior Publication Data

US 2002/0040160 A1 Apr. 4, 2002

Related U.S. Application Data

(62) Division of application No. 09/669,220, filed on Sep. 25, 2000, now Pat. No. 6,262,297.

(51) Int. Cl.$^7$ .............................. C07C 271/10
(52) U.S. Cl. ..................... 560/157; 560/160
(58) Field of Search ................ 560/157, 160

(56) References Cited

U.S. PATENT DOCUMENTS 4,520,167 A * 5/1985 Blank et al. ................ 525/131

* cited by examiner

*Primary Examiner*—Alan L. Rotman
*Assistant Examiner*—Ebenezer Sackey
(74) *Attorney, Agent, or Firm*—Gardere Wynne Sewell LLP

(57) ABSTRACT

A method of preparing hydroxyalkylcarbamates from six-membered cyclic carbonates. The method involves reacting a six-membered cyclic carbonate with anhydrous ammonia or aqueous ammonium hydroxide. The present invention also provides for hydroxyalkylcarbamates prepared from six-membered cyclic carbonates, and for coating compositions comprising hydroxyalkylcarbamates prepared according to the present invention.

6 Claims, No Drawings

PREPARATION OF HYDROXYALKYLCARBAMATES FROM SIX-MEMBERED CYCLIC CARBONATES

TECHNICAL FIELD

This is submitted as a divisional application of U.S. patent application Ser. No. 09/669,220 filed Sep. 25, 2000 now U.S. Pat. No. 6,262,297. The invention relates to carbamates, and more particularly, to hydroxyalkylcarbamates prepared from six-membered cyclic carbonates, methods of preparing such hydroxyalkylcarbamates, and coating compositions comprising hydroxyalkylcarbamates prepared according to the present invention.

BACKGROUND OF THE INVENTION

Carbamate derivatives are useful in a variety of applications, including, but not limited to, uses in pesticides, insecticides, antibiotics, and in the synthesis of polyurethanes. Polyurethanes prepared from carbamate derivatives, particularly, hydroxyalkylcarbamates, are useful in a variety of applications, including various coating technologies, as further discussed in *Low VOC Carbamate Functional Coatings Compositions for Automotive Topcoats*, Marvin L. Green, presented at the International Waterborne, High-Solids, and Powder Coating Symposium, Mar. 1–3, 2000, New Orleans, La., which is incorporated by reference.

Of particular interest in automotive clear coat technology, is the utilization of recently commercialized hydroxypropylcarbamate (HPC) compounds, which are typically prepared from five-membered carbonate rings. Unfortunately, the purification of such HPC compounds is complicated by the competing reverse reaction. Specifically, upon purification (i.e. removal of excess ammonia), such HPC compounds tend to revert back to their starting materials. As such, these HPC compounds tend to become easily contaminated if not handled properly.

Unlike carbamates produced from five-membered cyclic carbonates, carbamates produced from six-membered cyclic carbonates are easier to purify. In particular, upon purification (i.e. removal of excess ammonia), carbamates prepared from six-membered cyclic carbonates do not revert back to their starting materials. Presumably, this stability is due to the increased ring strain of six-membered cyclic carbonates, as compared with their five-membered counterparts. As such, hydroxyalkylcarbamates prepared from six-membered cyclic carbonates have superior handling characteristics, over hydroxyalkylcarbamates prepared from five-membered cyclic carbonates.

SUMMARY OF THE INVENTION

Accordingly, in one embodiment, the present invention is directed toward a method of preparing hydroxyalkylcarbamates from six-membered cyclic carbonates. The hydroxyalkylcarbamates of the present invention may be prepared by reacting a six-membered cyclic carbonate with anhydrous ammonia. The preparation may be represented by the following equation:

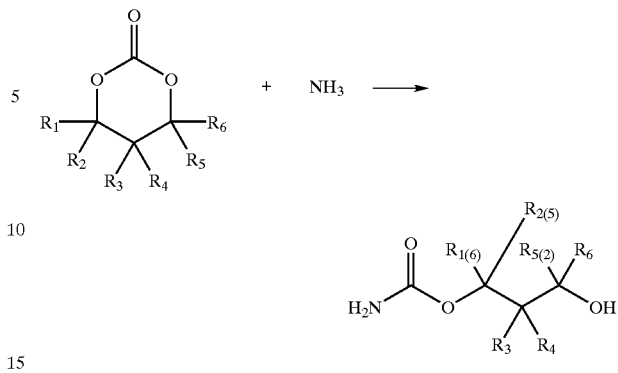

where $R_1$, $R_2$, $R_3$, $R_4$, $R_5$, and $R_6$ are each independently hydrogen or a linear or branched alkyl group with from about one to about six carbon atoms. The hydroxyalkylcarbamates of the present invention may also be prepared by reacting a six-membered cyclic carbonate with aqueous ammonium hydroxide. This preparation may be represented by the following equation:

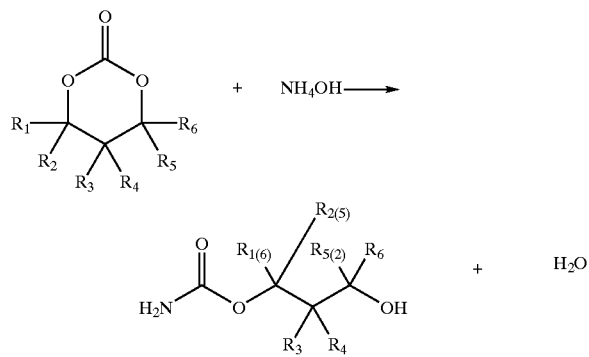

where $R_1$, $R_2$, $R_3$, $R_4$, $R_5$, and $R_6$ are each independently hydrogen or a linear or branched alkyl group with from about one to about six carbon atoms.

In another embodiment, the present invention provides for hydroxyalkylcarbamates prepared from six-membered cyclic carbonates. The hydroxyalkylcarbamates of the present invention have the following general structure:

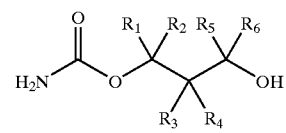

where $R_1$, $R_2$, $R_3$, $R_4$, $R_5$, and $R_6$ are each independently hydrogen or a linear or branched alkyl group with from about one to about six carbon atoms.

In another embodiment, the present invention provides for coating compositions comprising hydroxyalkylcarbamates prepared according to the present invention.

DETAILED DESCRIPTION OF THE PREFERRED EMBODIMENT

The present invention provides for methods of preparing hydroxyalkylcarbamates from six-membered cyclic carbonates. According to the methods of the present invention, hydroxyalkylcarbamates may be prepared by reacting a six-membered cyclic carbonate with either anhydrous ammonia or aqueous ammonium hydroxide.

According to a method of the present invention, hydroxyalkylcarbamates may be prepared by charging a reaction vessel with a six-membered cyclic carbonate with the following general structure:

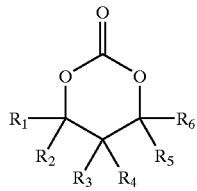

where $R_1$, $R_2$, $R_3$, $R_4$, $R_5$, and $R_6$ are each independently hydrogen or a linear or branched alkyl group with from about one to about six carbon atoms. Preferably, $R_1$, $R_2$, $R_3$, $R_4$, $R_5$, and $R_6$ are each independently hydrogen or an alkyl with from about one to about two carbon atoms. More preferably, at least four substituents of $R_1$–$R_6$ are hydrogen, and at least one substituent of $R_1$–$R_6$ is a methyl or ethyl group. After the reaction vessel has been charged with a six-membered cyclic carbonate, the vessel should be purged with an inert gas, such as, but not limited to, nitrogen, for at least thirty minutes. The reaction vessel should then be pressurized between about 50 psig to about 1000 psig; preferably, between about 50 psig to about 300 psig; and more preferably, between about 100 psig to about 250 psig with about 1.10 equivalents of anhydrous ammonia. Upon addition of the anhydrous ammonia, the reaction vessel should be heated to a temperature between about 25° C. to about 100° C.; preferably between about 45° C. to about 75° C.; and more preferably, about 55° C. for at least about two hours. During the progression of the reaction, a drop in the ammonia pressure will likely be observed. After heating, the reaction products should then be cooled, and purified. Any trace amounts of unreacted ammonia should be removed, preferably by vacuum, at about 3 torr. This method may be represented by the following equation:

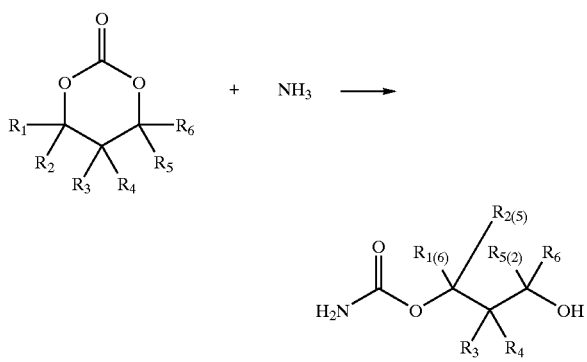

where $R_1$, $R_2$, $R_3$, $R_4$, $R_5$, and $R_6$ are each independently hydrogen or a linear or branched alkyl group with from about one to about six carbon atoms. Preferably, $R_1$, $R_2$, $R_3$, $R_4$, $R_5$, and $R_6$ are each independently hydrogen or an alkyl with from about one to about two carbon atoms. More preferably, at least four substituents of $R_1$–$R_6$ are hydrogen, and at least one substituent of $R_1$–$R_6$ is a methyl or ethyl group.

Alternatively, according to another method of the present invention, hydroxy-alkylcarbamates may be prepared by first mixing, in a reaction vessel, tetrahydrofuran (THF) and a six-membered cyclic carbonate with the following general structure:

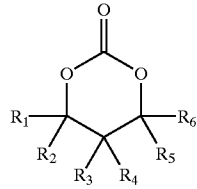

where $R_1$, $R_2$, $R_3$, $R_4$, $R_5$, and $R_6$ are each independently hydrogen or a linear or branched alkyl group with from about one to about six carbon atoms. Preferably, $R_1$, $R_2$, $R_3$, $R_4$, $R_5$, and $R_6$ are each independently hydrogen or an alkyl with from about one to about two carbon atoms. More preferably, at least four substituents of $R_1$–$R_6$ are hydrogen, and at least one substituent of $R_1$–$R_6$ is a methyl or ethyl group. After mixing, the vessel should be purged with an inert gas, such as, but not limited to, nitrogen, for at least thirty minutes. After purging, an aqueous ammonium hydroxide solution should be added slowly to the carbonate/THF solution (at atmospheric pressure). After the addition of the ammonium hydroxide is complete, the resulting mixture should then be heated to a temperature of about 60° C. for about two hours. Afterwards, the THF, water, and excess ammonium hydroxide should be evaporated. This method may be represented by the following equation:

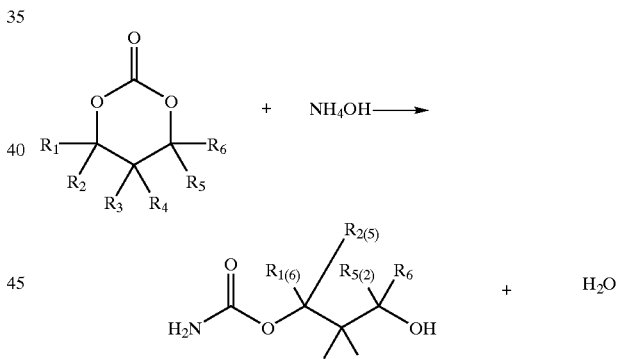

where $R_1$, $R_2$, $R_3$, $R_4$, $R_5$, and $R_6$ are each independently hydrogen or a linear or branched alkyl group with from about one to about six carbon atoms. Preferably, $R_1$, $R_2$, $R_3$, $R_4$, $R_5$, and $R_6$ are each independently hydrogen or an alkyl with from about one to about two carbon atoms. More preferably, at least four substituents of $R_1$–$R_6$ are hydrogen, and at least one substituent of $R_1$–$R_6$ is a methyl or ethyl group.

The present invention also provides for hydroxyalkylcarbamates prepared from six-membered cyclic carbonates. The hydroxyalkylcarbamates of the present invention may be prepared, as disclosed above, by reacting a six-membered cyclic carbonate with anhydrous ammonia or aqueous ammonium hydroxide, wherein the six-membered cyclic carbonate has the following general structure:

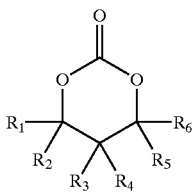

where $R_1$, $R_2$, $R_3$, $R_4$, $R_5$, and $R_6$ are each independently hydrogen or a linear or branched alkyl group with from about one to about six carbon atoms. Preferably, $R_1$, $R_2$, $R_3$, $R_4$, $R_5$, and $R_6$ are each independently hydrogen or an alkyl with from about one to about two carbon atoms. More preferably, at least four substituents of $R_1$–$R_6$ are hydrogen, and at least one substituent of $R_1$–$R_6$ is a methyl or ethyl group. The preparation of the hydroxyalkylcarbamates of the present invention may be represented by the following equations:

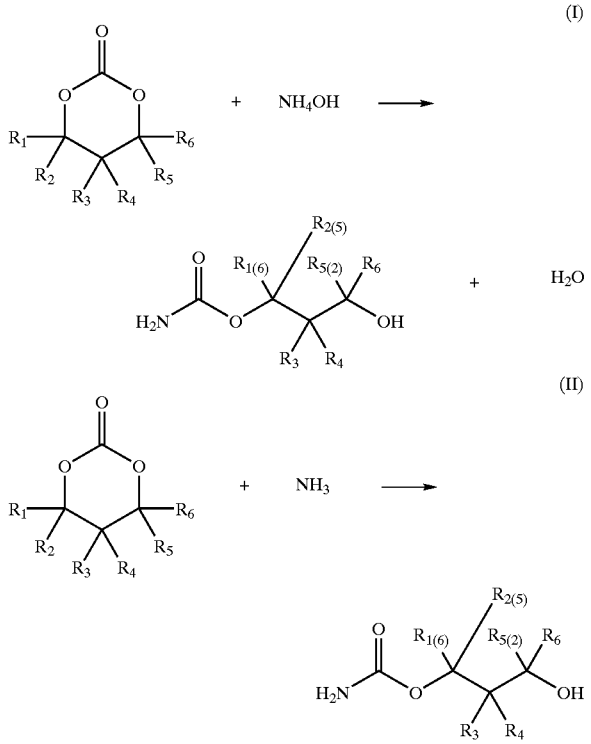

where $R_1$, $R_2$, $R_3$, $R_4$, $R_5$, and $R_6$ are each independently hydrogen or a linear or branched alkyl group with from about one to about six carbon atoms. Preferably, $R_1$, $R_2$, $R_3$, $R_4$, $R_5$, and $R_6$ are each independently hydrogen or an alkyl with from about one to about two carbon atoms. More preferably, at least four substituents of $R_1$–$R_6$ are hydrogen, and at least one substituent of $R_1$–$R_6$ is a methyl or ethyl group.

The hydroxyalkylcarbamates of the present invention may be used to prepare coating compositions using any suitable method know to those skilled in the art. Preferably, the hydroxyalkylcarbamates of the present invention may be used to prepare coating compositions in the manner described in U.S. Pat. No. 5,605,965, which is incorporated by reference. Generally, the coating compositions may be prepared by reacting a hydroxyalkylcarbamate of the present invention, under appropriate conditions, to produce a polymer with at least one carbamate functional group. The polymer may then be blended with a compound containing a plurality of functional groups that are reactive with the carbamate group. The reactive mixture may optionally be mixed with a solvent. A catalyst may optionally be used to enhance the curing reaction.

The coating compositions of the present invention may be used to coat an article by any number of techniques known in the art. These include, for example, spray coating, dip coating, roll coating, curtain coating, and the like. For automotive body panels, spray coating is preferred.

The coating compositions of the present invention are preferably subjected to conditions that promote the curing of the coating layers. Although various methods of curing may be used, heat curing is preferred.

The following examples are illustrative of the present invention, and are not intended to limit the scope of the invention in any way.

EXAMPLE 1

A 300 ml autoclave was charged with 100.0 grams of 5-methyl-1,3-dioxan-2-one (prepare by reacting diethylcarbonate and 2-methyl-1,3-propanediol, in the presence of potassium carbonate), and purged with nitrogen for thirty minutes. The autoclave was then pressurized to 200 psig with 16.1 grams of anhydrous ammonia (1.10 equivalents), and heated to a temperature of 55° C., during which time the ammonia pressure began to drop to 140 psig. The mixture was held at 55° C. for 2.5 hours, and then cooled. Upon cooling to 45° C., the autoclave pressure was 132 psig. The resulting product was a viscous yellow liquid, which was then heated to 45° C., on a rotary evaporator, at 3 torr, to remove the trace amounts of unreacted ammonia. The resulting product was identified as 2-methyl-3-hydroxypropylcarbamate (94.5%) and 2-methyl-1,3-propanediol (5.0%) by LC and LC/MS.

EXAMPLE 2

A 300 ml autoclave was charged with 100.0 grams of 4-methyl-1,3-dioxan-2-one (prepare by reacting diethylcarbonate and 1,3-butanediol, in the presence of potassium carbonate), and purged with nitrogen for thirty minutes. The autoclave was then pressurized to 195 psig with 16.1 grams of anhydrous ammonia (1.10 equivalents), and heated to a temperature of 55° C., during which time the ammonia pressure began to drop to 105 psig. The mixture was held at 55° C. for 2.5 hours, and then cooled. Upon cooling to 45° C., the autoclave pressure was 101 psig. The resulting product was a viscous yellow liquid, which was then heated to 45° C., on a rotary evaporator, at 3 torr, to remove the trace amounts of unreacted ammonia. The resulting product was identified to be a mixture of two isomers, namely, 1-methyl-3-hydroxypropylcarbamate (49.2%) and 3-methyl-3-hydroxypropylcarbamate (46.6%), and a small amount of 1,3-butanediol (2.5%) by LC and LC/MS.

EXAMPLE 3

83.7 grams (0.721 mol) of 5-methyl-1,3-dioxan-2-one were placed in a one liter round bottom flask that was equipped with a dropping funnel, a thermocouple probe, a magnetic stir bar. The carbonate was then diluted with 100 ml of THF. Then, 91.22 grams (0.764 mol) of an aqueous ammonium hydroxide (29% wt.) solution were placed in the dropping funnel. After purging the system with nitrogen for about thirty minutes, the ammonium hydroxide solution was slowly added to the carbonate/THF solution. An exotherm for the reaction was observed (about 47° C.). After all the ammonium hydroxide had been added to the carbonate/THF mixture, the resulting mixture was heated at a temperature of about 60° C. for about two hours. After cooling, the resulting mixture was heated to 45° C. in a rotary evaporator at 3 torr to remove the water, THF, and excess ammonium hydroxide. The resulting product was a water-white liquid product (72.3 grams). LC/MS and LC analysis determined that the product contained 92.8% 2-methyl-3-hydroxypropylcarbamate and 6.9% 2-methyl-1,3-propanediol.

EXAMPLE 4A (PROPHETIC)

The hydroxyalkylcarbamate prepared in Example 1 is then reacted under appropriate conditions to produce a polymer with at least one carbamate functional group. The polymer is then blended with a compound containing a plurality of functional groups that are reactive with the carbamate group. The reactive mixture is optionally mixed with a solvent. A catalyst is optionally used to enhance the curing reaction.

EXAMPLE 4B (PROPHETIC)

The hydroxyalkylcarbamate prepared in Example 2 is then reacted under appropriate conditions to produce a polymer with at least one carbamate functional group. The polymer is then blended with a compound containing a plurality of functional groups that are reactive with the carbamate group. The reactive mixture is optionally mixed with a solvent. A catalyst is optionally used to enhance the curing reaction.

EXAMPLE 4C (PROPHETIC)

The hydroxyalkylcarbamate prepared in Example 3 is then reacted under appropriate conditions to produce a polymer with at least one carbamate functional group. The polymer is then blended with a compound containing a plurality of functional groups that are reactive with the carbamate group. The reactive mixture is optionally mixed with a solvent. A catalyst is optionally used to enhance the curing reaction.

EXAMPLE 5 (PROPHETIC)

The coating compositions prepared in Examples 4a, 4b, and 4c are sprayed on steel panels that have been previously sprayed with a basecoat and flashed. The panels are baked. The panels are then subjected to weathering conditions, and exhibit significantly reduced environmental etch versus panels coated with conventional clearcoats.

Although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A method for preparing a hydroxyalkylcarbamate composition comprising the step of reacting aqueous ammonium hydroxide and a cyclic carbonate, wherein the cyclic carbonate has the following general structure:

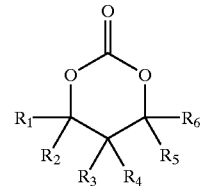

where $R_1$, $R_2$, $R_3$, $R_4$, $R_5$, and $R_6$ are each independently hydrogen or a linear or branched alkyl group having one to six carbon atoms.

2. The method of claim 1, wherein the step of reacting is conducted at atmospheric pressure.

3. The method of claim 1, further comprising the step of purifying the hydroxy-alkylcarbamate composition.

4. The method of claim 3, wherein the step of purifying is conducted using evaporation.

5. The method of claim 1, wherein $R_1$, $R_2$, $R_3$, $R_4$, $R_5$, and $R_6$ are each independently hydrogen or an alkyl having one to two carbon atoms.

6. The method of claim 1, wherein at least four substituents of $R_1$–$R_6$ are hydrogen, and at least one substituent of $R_1$–$R_6$ is a methyl or ethyl group.

* * * * *